(12) United States Patent
Collingwood et al.

(10) Patent No.: US 8,597,912 B2
(45) Date of Patent: Dec. 3, 2013

(54) METHODS AND COMPOSITIONS FOR GENERATION OF BAX-AND BAK-DEFICIENT CELL LINES

(75) Inventors: Trevor Collingwood, Novato, CA (US); Philip D. Gregory, Orinda, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 586 days.

(21) Appl. No.: 12/456,043

(22) Filed: Jun. 10, 2009

(65) Prior Publication Data

US 2010/0003756 A1 Jan. 7, 2010

Related U.S. Application Data

(60) Provisional application No. 61/131,579, filed on Jun. 10, 2008, provisional application No. 61/133,792, filed on Jul. 2, 2008.

(51) Int. Cl.
*C12N 15/00* (2006.01)
*C12P 21/00* (2006.01)

(52) U.S. Cl.
USPC ....... 435/69.7; 435/252.3; 435/440; 435/455; 530/350

(58) Field of Classification Search
USPC ........ 435/69.1, 252.3, 6.1, 440, 455; 530/350
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox et al. | |
| 6,599,692 B1 | 7/2003 | Case | |
| 6,607,882 B1 | 8/2003 | Cox, III et al. | |
| 6,689,558 B2 | 2/2004 | Case | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,153,949 B2 | 12/2006 | Kim et al. | |
| 7,163,824 B2 | 1/2007 | Cox, III et al. | |
| 2003/0091982 A1 | 5/2003 | Zong et al. | |
| 2005/0064474 A1 | 3/2005 | Urnov et al. | |
| 2005/0214851 A1 | 9/2005 | Arts et al. | |
| 2005/0245476 A1 | 11/2005 | Collingwood | |
| 2006/0024726 A1 | 2/2006 | Liu et al. | |
| 2006/0063231 A1 | 3/2006 | Li et al. | |
| 2006/0188987 A1 | 8/2006 | Guschin et al. | |
| 2007/0218528 A1 | 9/2007 | Miller | |
| 2008/0015164 A1 | 1/2008 | Collingwood | |
| 2008/0131962 A1 | 6/2008 | Miller | |
| 2008/0159996 A1 | 7/2008 | Ando et al. | |
| 2009/0068164 A1 | 3/2009 | Segal | |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2007/014275 A2 | 1/2007 |
| WO | WO 2007/139898 A2 | 12/2007 |
| WO | WO 2007/139982 A2 | 12/2007 |
| WO | WO 2008/076290 A2 | 6/2008 |

OTHER PUBLICATIONS

Miller et al., An improved zinc-finger nuclease architecture for highly specific genome editingNature Biotechnology 25, 778-785 (2007.*
Voet, Biochemistry John Wiley and Sons, 1990, pp. 126-128.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-506.*
Rudinger, J., "Characteristics of the amino acids as components of a peptide hormone sequence",in Peptide Hormones, University Park Press: Baltimore, MD, pp. 1-7, 1976.*
Kimchi-Sarfaty Cet al., A "silent" polymorphism in the MDR1 gene changes substrate specificity.Science. Jan. 26, 2007;315(5811):525-8.*
Greisman HA etal., Science. Jan. 31, 1997;275(5300):657-61.A general strategy for selecting high-affinity zinc finger proteins for diverse DNA target sites.*
Tan et al Proc Natl Acad Sci U S A. Oct. 14, 2003;100(21):11997-2002. Epub Sep. 26, 2003. Zinc-finger protein-targeted gene regulation: genomewide single-gene specificity.*
Falke, et al., "Design of Artifical Transcription Factors to Seletively Regulate the Pro-apoptotic Bax Gene," *Nucleic Acids Research* 31:1-8 (2003).
Nowak, et al., "Complete Sequence of Chromosomel of Burkholderia Phytofirmans PSJN," Genbank Accession No. YP_001894925 (2008).
Beerli, et al., "Engineering Polydactyl Zinc-Finger Transcription Factors," *Nature Biotechnology* 20:135-141 (2002).
Bitinate, et al., "Foki Dimerization is Required for DNA Cleavage," *PNAS USA* 95:10570-10575 (1998).
Choo, et al., "Advances in Zinc Finger Engineering," *Curr. Opin. Struct. Biol.* 10:411-416 (2000).

(Continued)

*Primary Examiner* — Maria Leavitt
(74) *Attorney, Agent, or Firm* — Pasternak Patent Law; Dahna S. Pasternak

(57) ABSTRACT

Disclosed herein are methods and compositions for generation of Bak- and/or Bax-deficient cell lines using engineered nucleases.

16 Claims, 9 Drawing Sheets

(56) References Cited

OTHER PUBLICATIONS

Grimes, et al., "The GFI-1 Protooncoprotein Represses Bax Expression and Inhibits T-Cell Death," *PNAS USA* 93:14569-14573 (1996).

Isalan et al., "A Rapid, Generally Applicable Method to Engineer Zinc Fingers Illustrated by Targeting the HIV-1 Promoter," *Nat Biotechnol* 19:656-660 (2001).

Kim, et al., "Chimeric Restriction Endonuclease," *PNAS USA* 91:883-887 (1994).

Kim, et al., "Insertion and Deletion Mutants of Foki Restriction Endonuclease," *J. Biol. Chem.* 269:31978-31981 (1994).

Li, et al., "Functional Domains in Fok I Restriction Endonuclease," *PNAS USA* 89:4275-4279 (1992).

Li, et al., "Alteration of the Cleavage Distance of Fok I Restriction Endonuclease by Insertion Mutagenesis," *PNAS USA* 90:2764-2768 (1993).

Mandic, et al., "Cisplatin Induces the Proapoptotic Conformation of Bak in a Deltamekk1-Dependent Manner," *Mol Cell Biol* 21:3684-3691 (2001).

Pabo, et al., "Design and Selection of Novel CYS2-HIS2 Zinc Finger Proteins," *Ann. Rev. Biochem.* 70:313-340 (2001).

Segal, et al., "Custom DNA-Binding Proteins Come of Age: Polydactyl Zinc-Finger Proteins," *Curr. Opin. Biotechnol.* 12:632-637 (2001).

Urnov, et al., "Highly Efficient Endogenous Human Gene Correction Using Designed Zinc-Finger Nucleases," *Nature* 435(7042):646-651 (2005).

Zhang, et al., "Role of Bax in the Apoptotic Response to Anticancer Agents," *Science* 290:989-992 (2000).

Cost, et al., "Bak and Bax Deletion Using Zinc-Finger Nucleases Yields Apoptosis-Resistant Cho Cells," *Biotechnology and Bioengineering* 105:330-340 (2010).

Cristea, et al., "Dissection of Splicing Regulation at an Endogenous Locus by Zinc-Finger Nuclease-Mediated Gene Editing," PLOS One 6: E16961 (2011).

Dhanasekaran, et al., "Designer Zinc Finger Proteins: Tools for Creating Artificial DNA-Binding Functional Proteins," *Acc. Chem. Res.* 39:45-52 (2006).

Rathmell, et al., "Deficiency in Bak and Bax Perturbs Thymic Selection and Lymphoid Homeostasis," *Nature Immunology* 3:932-939 (2002).

\* cited by examiner

FIG. 1:
Genotype of *BAK KO* CHO-K1 cells

```
             39F/38R    CAGTGCTGCCAACCAAGGCCTGAAAG ATG GCGTCTCTGGACAAGGACC
          1  Bak 8H6-1  CAGTG :: :: :: :: :: :: :: :: :: :: ::CTGGACAAGGACC
Allele A  1  Bak 8H6-3  CAGTG :: :: :: :: :: :: :: :: :: :: ::CTGGACAAGGACC
          1  Bak 8H6-2  CAGTGCTGCCAACCAAGGCC :: :: :: :: ::CATCTGGACAAGGACC
Allele B  1  Bak 8H6-4  CAGTGCTGCCAACCAAGGCC :: :: :: :: ::CATCTGGACAAGGACC
          1  Bak 8D4-1  CAGTGNTGCCAACCAAGG :: :: :: :: :: ::ACAAG  ACC
Allele A  1  Bak 8D4-2  CAGTGCTGCCAACCAAGG :: :: :: :: :: ::ACAAGGACC
          1  Bak 8D4-3  CAGTGCTGCCAACCAAGG :: :: :: :: :: ::ACAAGGACC
Allele B  1  Bak 8D4-4  CAGTGCTGCCAACCAAGG :: :: :: :: :: ::ACAAGGACC
```

☐ = start codon

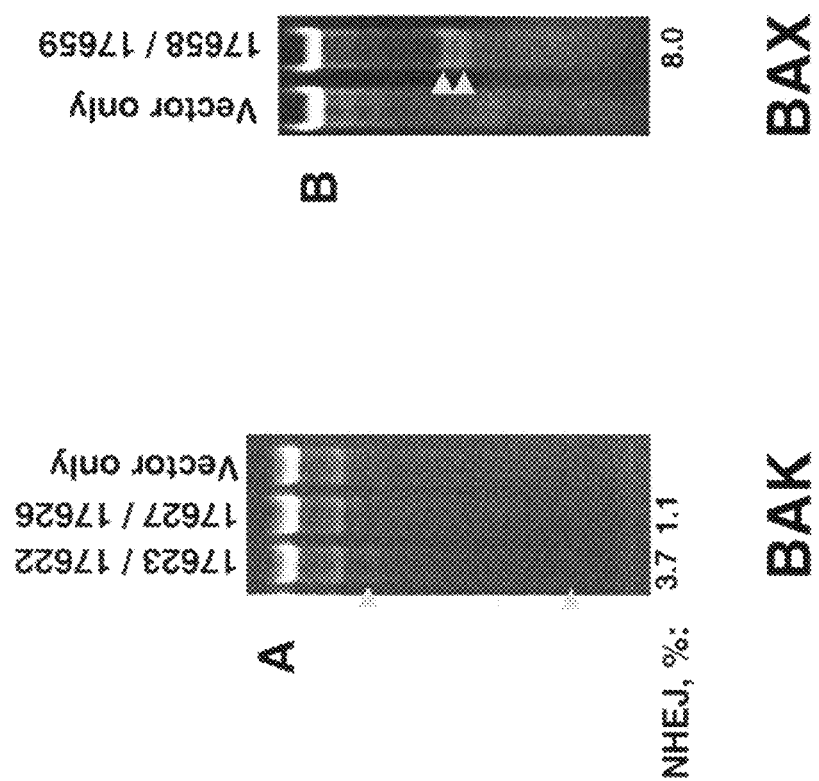

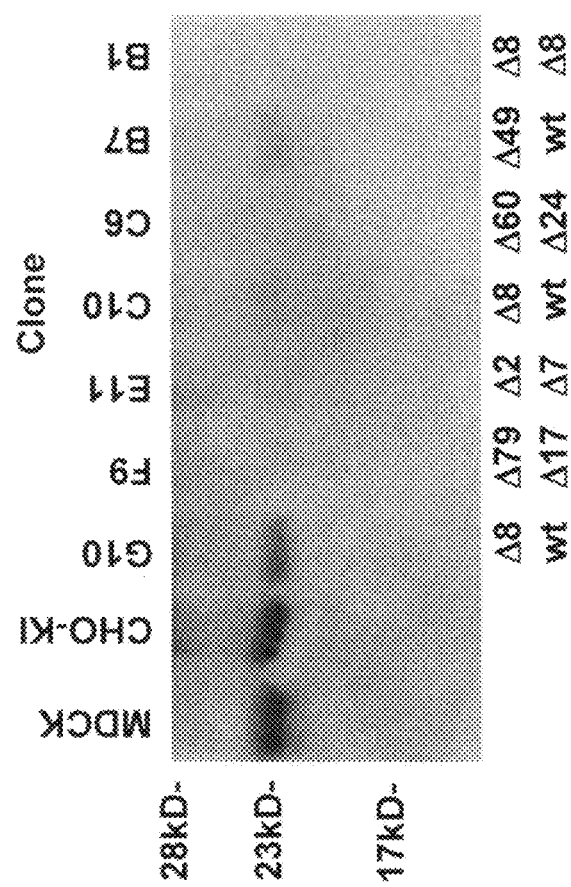

FIG. 2D

Bax

*BAX*-only single KO: Δ30, +1

*BAX* alleles in *BAK*-deleted clones:

wt wt wt wt wt
Δ1 +4 Δ7 Δ8 +1

(heterozygotes)

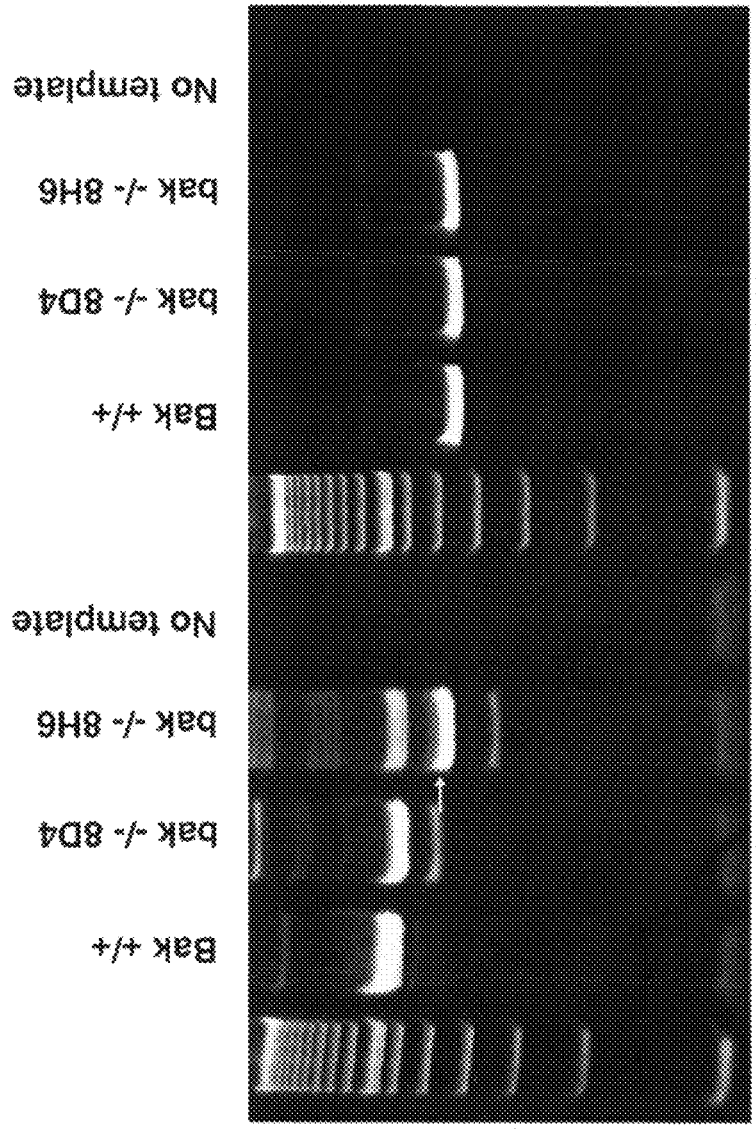
FIG. 3: Bak and Bax RNA analysis: exon skipping in a BAK KO clone

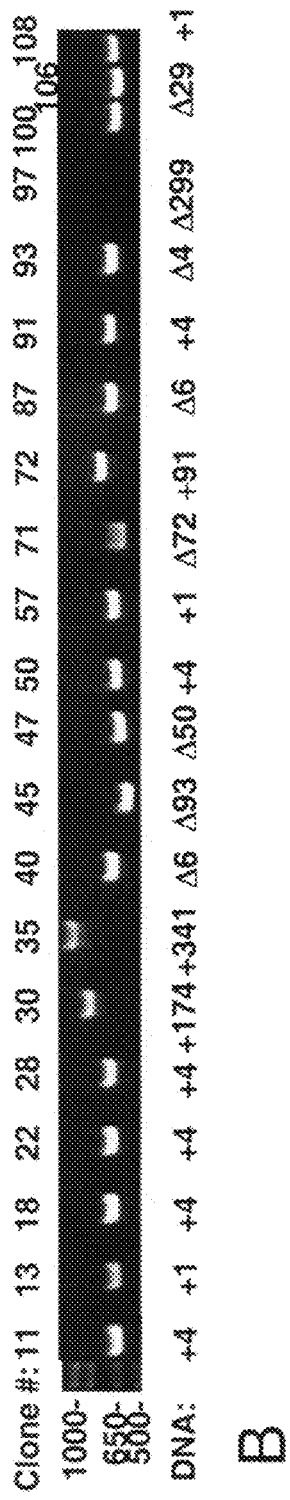
FIG. 4: Genotype of Bax KO clones in Bak KO clone 8H6

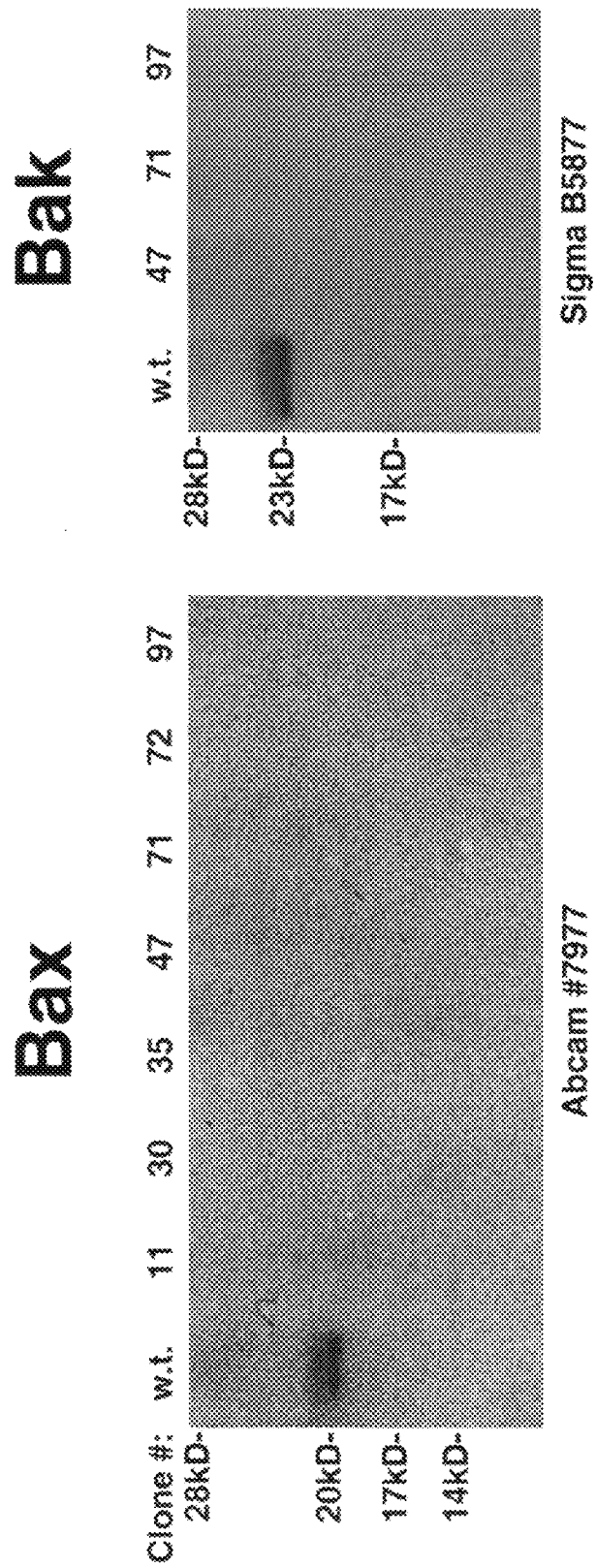
FIG. 5: Elimination of Bax and Bak protein in Bax/Bak double-KO cells

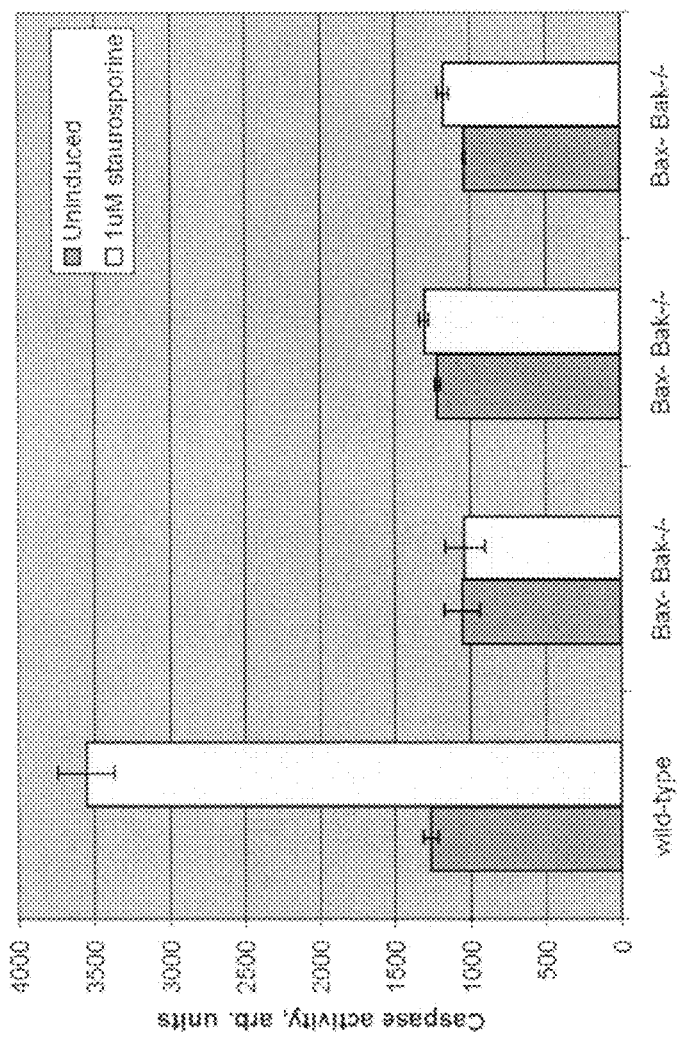
FIG. 6: Bax/Bak KO prevents apoptosis

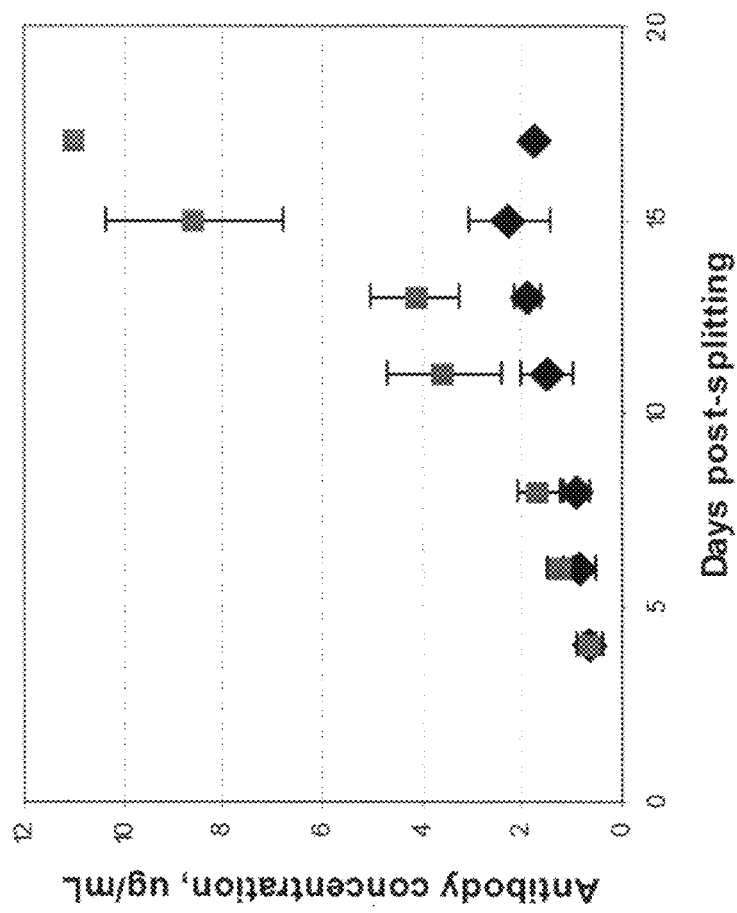
FIG. 7: Bax/Bak KO results in increased mAb production

SEQUENCE LISTING

```
<160> NUMBER OF SEQ ID NOS: 94

<210> SEQ ID NO 1
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 1

Arg Ser Asp His Leu Ser Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 2

Asp Arg Ser His Leu Ala Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic zinc finger nuclease targeted to
      BAK/BAX

<400> SEQUENCE: 3

Gln Ser Ser His Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 4

Arg Ser Asp Asn Leu Arg Glu
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 5

Arg Ser Ala Asn Leu Ser Val
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 6

Asp Arg Ala Asn Leu Ser Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic zinc finger nuclease targeted to
      BAK/BAX

<400> SEQUENCE: 7

Asn Arg Thr Asp Leu Ile Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic zinc finger nuclease targeted to
      BAK/BAX

<400> SEQUENCE: 8

Thr Ser Ser Asn Leu Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 9

Arg Ser Asp His Leu Thr Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 10

Arg Ser Asp His Leu Ser Glu
```

```
<210> SEQ ID NO 11
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 11

Arg Asn Asp Asn Arg Lys Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 12

Gln Ser Gly His Leu Gln Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 13

Gln Ser Gly His Leu Ser Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 14

Arg Ser Asp Ser Leu Ser Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 15

Asp Arg Ser Ser Arg Thr Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 16

Arg Ser Asp Asp Leu Thr Arg
1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 17

Arg Ser Asp Ala Leu Ala Arg
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic linker sequence

<400> SEQUENCE: 18

Thr Gly Glu Lys Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic linker sequence

<400> SEQUENCE: 19

Thr Gly Gln Lys Pro
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic linker sequence

<400> SEQUENCE: 20

Thr Gly Ser Gln Lys Pro
1               5

<210> SEQ ID NO 21
<211> LENGTH: 12
<212> TYPE: DNA
<213> ORGANISM: Artificial Sequence
<220> FEATURE:
<223> OTHER INFORMATION: Synthetic oligonucleotide:  SBS 10077

<400> SEQUENCE: 21
cagggtggct gg                                                         12

<210> SEQ ID NO 22
<211> LENGTH: 12
<212> TYPE: DNA
<213> ORGANISM: Artificial Sequence
<220> FEATURE:
<223> OTHER INFORMATION: Synthetic oligonucleotide:  SBS 10079

<400> SEQUENCE: 22
gatccagaca ag                                                         12

<210> SEQ ID NO 23
<211> LENGTH: 15
<212> TYPE: DNA
```

```
<213> ORGANISM: Artificial Sequence
<220> FEATURE:
<223> OTHER INFORMATION: Synthetic oligonucleotide: SBS 11205

<400> SEQUENCE: 23
ggaggaaagg ggtgg                                                    15

<210> SEQ ID NO 24
<211> LENGTH: 12
<212> TYPE: DNA
<213> ORGANISM: Artificial Sequence
<220> FEATURE:
<223> OTHER INFORMATION: Synthetic oligonucleotide: SBS 10350

<400> SEQUENCE: 24
gtggcggccc tg                                                       12

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide: GJC 39F

<400> SEQUENCE: 25
tcaagaggtt tcatggcgag                                               20

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide: GJC 38R

<400> SEQUENCE: 26
ttctctctct tgtgcttatg g                                             21

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide: GJC 24F

<400> SEQUENCE: 27
catctcacat ctggaccaca gccg                                          24

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide: GJC 25R

<400> SEQUENCE: 28
ctggaactct gtgtcgtatc tccgg                                         25

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide: GJC 12F

<400> SEQUENCE: 29
cttcttccgg gtggcagctg                                               20
```

```
<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide: GJC 23R

<400> SEQUENCE: 30
cccgaagtat gagaggaggc catc                                          24

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide: GJC 52F

<400> SEQUENCE: 31
cagaggaatg aaagcaaagg                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide: GJC 114R

<400> SEQUENCE: 32
tgaaccaggc tgggagattt                                               20

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide: SBS 14238

<400> SEQUENCE: 33
tttcaggcct tggttggc                                                 18

<210> SEQ ID NO 34
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 34

Asp Arg Ser His Leu Ser Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 35

Thr Ser Gly Ser Leu Thr Arg
1               5

<210> SEQ ID NO 36
<211> LENGTH: 7
<212> TYPE: PRT
<213> ORGANISM: Artificial Sequence
<220> FEATURE:
```

-continued

<223> OTHER INFORMATION: Synthetic zinc finger nuclease targeted to BAK

<400> SEQUENCE: 36

Arg Ser Asp Asn Leu Ser Glu
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 37

His Ser Asn Ala Arg Lys Thr
1               5

<210> SEQ ID NO 38
<211> LENGTH: 12
<212> TYPE: DNA
<213> ORGANISM: Artificial Sequence
<220> FEATURE:
<223> OTHER INFORMATION: Synthetic oligonucleotide: SBS 10526

<400> SEQUENCE: 38
cgtctggaca ag                                                         12

<210> SEQ ID NO 39
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 39

Arg Ser Asp Asn Leu Ser Val
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 40

Asp Arg Ser Asn Leu Thr Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 41

Arg Ser Asp Thr Leu Ser Glu
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 42

Arg Ser Gln Thr Arg Lys Thr
1               5

<210> SEQ ID NO 43
<211> LENGTH: 15
<212> TYPE: DNA
<213> ORGANISM: Artificial Sequence
<220> FEATURE:
<223> OTHER INFORMATION: Synthetic oligonucleotide: SBS 17658

<400> SEQUENCE: 43
gtcctggatc cagcc                                                   15

<210> SEQ ID NO 44
<211> LENGTH: 16
<212> TYPE: DNA
<213> ORGANISM: Artificial Sequence
<220> FEATURE:
<223> OTHER INFORMATION: Synthetic oligonucleotide: SBS 17659

<400> SEQUENCE: 44
ggttgggtga ggcctg                                                  16

<210> SEQ ID NO 45
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 45

Asp Arg Ser Asp Leu Ser Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 46

Arg Ser Asp Thr Leu Ser Gln
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 47

Asp Arg Ser Ala Arg Thr Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 48

Arg Ser Asp Ala Leu Ser Val
1               5

```
<210> SEQ ID NO 49
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 49

Asp Ser Ser His Arg Thr Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic zinc finger nuclease targeted to
      BAK/BAX

<400> SEQUENCE: 50

Gln Asn Ala His Arg Lys Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic zinc finger nuclease targeted to BAX

<400> SEQUENCE: 51

Thr Ser Gly His Leu Ser Arg
1               5

<210> SEQ ID NO 52
<211> LENGTH: 15
<212> TYPE: DNA
<213> ORGANISM: Artificial Sequence
<220> FEATURE:
<223> OTHER INFORMATION: Synthetic oligonucleotide:  SBS 17622

<400> SEQUENCE: 52
aatgatgcag catga                                                    15

<210> SEQ ID NO 53
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 53

Gln Ser Gly Asp Leu Thr Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 54

Gln Ser Ser Asn Leu Ala Arg
1               5

<210> SEQ ID NO 55
```

```
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 55

Thr Ser Ser Asn Arg Lys Thr
1               5

<210> SEQ ID NO 56
<211> LENGTH: 18
<212> TYPE: DNA
<213> ORGANISM: Artificial Sequence
<220> FEATURE:
<223> OTHER INFORMATION: Synthetic oligonucleotide:  SBS 17623

<400> SEQUENCE: 56
ccggtggatc gcgcagag                                                 18

<210> SEQ ID NO 57
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 57

Arg Ser Asp Asn Leu Ala Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 58

Asp Asn Arg Gln Leu Ile Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 59

Arg Ser Asp Thr Leu Ser Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 60

Arg Asn Asp Asp Arg Ile Thr
1               5

<210> SEQ ID NO 61
<211> LENGTH: 16
<212> TYPE: DNA
<213> ORGANISM: Artificial Sequence
```

-continued

<220> FEATURE:
<223> OTHER INFORMATION: Synthetic oligonucleotide: SBS 17627

<400> SEQUENCE: 61
aggggtggct gggtag    16

<210> SEQ ID NO 62
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 62

Arg Ser Asp Asn Leu Thr Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 63

Arg Ser Asp His Leu Ser Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 64

Gln Ser Ser Asp Leu Arg Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 65

Arg Ser Asp His Leu Thr Gln
1               5

<210> SEQ ID NO 66
<211> LENGTH: 18
<212> TYPE: DNA
<213> ORGANISM: Artificial Sequence
<220> FEATURE:
<223> OTHER INFORMATION: Synthetic oligonucleotide: SBS 17626

<400> SEQUENCE: 66
gatccaccgg gcaatgca    18

<210> SEQ ID NO 67
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 67

Gln Ser Gly Ser Leu Thr Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 68

Asp Arg Ser His Leu Thr Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic zinc finger nuclease targeted to BAK

<400> SEQUENCE: 69

Arg Ser Asp Asp Arg Lys Thr
1               5

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide: YS 13F

<400> SEQUENCE: 70
ctcctttcac agagatgcag                                           20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide: YS 14R

<400> SEQUENCE: 71
caggagagac agagtggtca                                           20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide: YS 21F

<400> SEQUENCE: 72
aaaaagactg cagtggcgca                                           20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide: YS 22R

<400> SEQUENCE: 73
tcacccagag gtcaatggat                                           20

<210> SEQ ID NO 74

```
<211> LENGTH: 6
<212> TYPE: PRT
<213> ORGANISM: Artificial Sequence
<220> FEATURE:
<223> OTHER INFORMATION: Synthetic oligonucleotide:  linker sequence

<400> SEQUENCE: 74

Thr Gly Gly Gln Arg Pro
1               5

<210> SEQ ID NO 75
<211> LENGTH: 46
<212> TYPE: DNA
<213> ORGANISM: Artificial Sequence
<220> FEATURE:
<223> OTHER INFORMATION: Synthetic sequence from Fig. 1:  39F[3]8R

<400> SEQUENCE: 75
cagtgctgcc aaccaaggcc tgaaagatgg cgtctggaca aggacc            46

<210> SEQ ID NO 76
<211> LENGTH: 18
<212> TYPE: DNA
<213> ORGANISM: Artificial Sequence
<220> FEATURE:
<223> OTHER INFORMATION: Synthetic sequence from Fig. 1:  Bak 8H6-1/Bak
      8H6-3

<400> SEQUENCE: 76
cagtgctgga caaggacc                                            18

<210> SEQ ID NO 77
<211> LENGTH: 36
<212> TYPE: DNA
<213> ORGANISM: Artificial Sequence
<220> FEATURE:
<223> OTHER INFORMATION: Synthetic sequence from Fig. 1:  Bak 8H6-2/Bak
      8H6-4

<400> SEQUENCE: 77
cagtgctgcc aaccaaggcc catctggaca aggacc                        36

<210> SEQ ID NO 78
<211> LENGTH: 27
<212> TYPE: DNA
<213> ORGANISM: Artificial Sequence
<220> FEATURE:
<223> OTHER INFORMATION: Synthetic sequence from Fig. 1:  Bak 8D4-1
<220> FEATURE:
<221> NAME/KEY: misc_feature
<222> LOCATION: (6)..(6)
<223> OTHER INFORMATION: n is a, c, g, or t

<400> SEQUENCE: 78
cagtgntgcc aaccaaggac aaggacc                                  27

<210> SEQ ID NO 79
<211> LENGTH: 27
<212> TYPE: DNA
<213> ORGANISM: Artificial Sequence
<220> FEATURE:
<223> OTHER INFORMATION: Synthetic sequence from Fig. 1:  Bak 8D4-2/Bak
      8D4-3/Bak 8D4-4

<400> SEQUENCE: 79
cagtgctgcc aaccaaggac aaggacc                                  27

<210> SEQ ID NO 80
```

```
<211> LENGTH: 111
<212> TYPE: DNA
<213> ORGANISM: Artificial Sequence
<220> FEATURE:
<223> OTHER INFORMATION: Synthetic sequence from Fig. 4B: 52F114R

<400> SEQUENCE: 80
tggacactgg acttcctccg agagcggctg cttgtctgga tccaagacca gggtggctgg    60
gtgagacccc ttagtccttg tcacacttta gactagtggt tctcaaactt c            111

<210> SEQ ID NO 81
<211> LENGTH: 115
<212> TYPE: DNA
<213> ORGANISM: Artificial Sequence
<220> FEATURE:
<223> OTHER INFORMATION: Synthetic sequence from Fig. 4B: 11, 18, 22,
      28, 50, and 91

<400> SEQUENCE: 81
tggacactgg acttcctccg agagcggctg cttgtctgga tccaagaaag accagggtgg    60
ctgggtgaga ccccttagtc cttgtcacac tttagactag tggttctcaa acttc         115

<210> SEQ ID NO 82
<211> LENGTH: 112
<212> TYPE: DNA
<213> ORGANISM: Artificial Sequence
<220> FEATURE:
<223> OTHER INFORMATION: Synthetic sequence from Fig. 4B: 13

<400> SEQUENCE: 82
tggacactgg acttcctccg agagcggctg cttgtctgga tccaagaacc agggtggctg    60
ggtgagaccc cttagtcctt gtcacacttt agactagtgg ttctcaaact tc            112

<210> SEQ ID NO 83
<211> LENGTH: 108
<212> TYPE: DNA
<213> ORGANISM: Artificial Sequence
<220> FEATURE:
<223> OTHER INFORMATION: Synthetic sequence from Fig. 4B: 30

<400> SEQUENCE: 83
tggacactgg acttcctccg agagcggctg cttgtctgga ttgacgcaga taaaattcca    60
tttcatccct actatactat taaagaccta ctaggagcct tcatgcta                 108

<210> SEQ ID NO 84
<211> LENGTH: 110
<212> TYPE: DNA
<213> ORGANISM: Artificial Sequence
<220> FEATURE:
<223> OTHER INFORMATION: Synthetic sequence from Fig. 4B: 35

<400> SEQUENCE: 84
tggacactgg acttcctccg agagcggctg cttgtctgga tccaagagac tctgctggcg    60
ctctaccttg tccctcatgt tctgtgtggc tttagggaag aacccttat               110

<210> SEQ ID NO 85
<211> LENGTH: 105
<212> TYPE: DNA
<213> ORGANISM: Artificial Sequence
<220> FEATURE:
<223> OTHER INFORMATION: Synthetic sequence from Fig. 4B: 40, 87

<400> SEQUENCE: 85
tggacactgg acttcctccg agagcggctg cttgtctgga tccagggtgg ctgggtgaga    60
```

```
cccottagtc cttgtcacac tttagactag tggttctcaa acttc            105

<210> SEQ ID NO 86
<211> LENGTH: 61
<212> TYPE: DNA
<213> ORGANISM: Artificial Sequence
<220> FEATURE:
<223> OTHER INFORMATION: Synthetic sequence from Fig. 4B: 46

<400> SEQUENCE: 86
ggtgagctgg gtgagacccc ttagtccttg tcacacttta gactagtggt tctcaaactt    60
c                                                                    61

<210> SEQ ID NO 87
<211> LENGTH: 65
<212> TYPE: DNA
<213> ORGANISM: Artificial Sequence
<220> FEATURE:
<223> OTHER INFORMATION: Synthetic sequence from Fig. 4B: 47

<400> SEQUENCE: 87
tggacactgg acttcctccg agagcggctg cttgtctgga tccagactag tggttctcaa    60
acttc                                                                65

<210> SEQ ID NO 88
<211> LENGTH: 114
<212> TYPE: DNA
<213> ORGANISM: Artificial Sequence
<220> FEATURE:
<223> OTHER INFORMATION: Synthetic sequence from Fig. 4B: 57

<400> SEQUENCE: 88
tggacactgg acttcctccg agagcggctg cttgtctgga tccaagaaga ccagggtggc    60
tgggtgagac cccttagtcc ttgtcacact ttagactagt ggttctcaaa cttc         114

<210> SEQ ID NO 89
<211> LENGTH: 43
<212> TYPE: DNA
<213> ORGANISM: Artificial Sequence
<220> FEATURE:
<223> OTHER INFORMATION: Synthetic sequence from Fig. 4B: 71

<400> SEQUENCE: 89
tggacactgg acttcctccg agagcggctg cttgtcaaac ttc                      43

<210> SEQ ID NO 90
<211> LENGTH: 114
<212> TYPE: DNA
<213> ORGANISM: Artificial Sequence
<220> FEATURE:
<223> OTHER INFORMATION: Synthetic sequence from Fig. 4B: 72

<400> SEQUENCE: 90
tggacactgg acttcctccg agagcggctg cttgtctgga tccatgaggg cagagtatct    60
acagaaatat ttgtaatctt tctactgata atactcatct cttcctaact catg         114

<210> SEQ ID NO 91
<211> LENGTH: 111
<212> TYPE: DNA
<213> ORGANISM: Artificial Sequence
<220> FEATURE:
<223> OTHER INFORMATION: Synthetic sequence from Fig. 4B: 93
<220> FEATURE:
<221> NAME/KEY: misc_feature
```

```
<222> LOCATION: (51)..(51)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t

<400> SEQUENCE: 91
tggacactgg acttcctccg agagcggctg cttgtctgga tccaagacca nggtggctgg      60
gtgagacccc ttantccttg tcacacttta nactantggt tctcaaactt c              111

<210> SEQ ID NO 92
<211> LENGTH: 19
<212> TYPE: DNA
<213> ORGANISM: Artificial Sequence
<220> FEATURE:
<223> OTHER INFORMATION: Synthetic sequence from Fig. 4B: 97

<400> SEQUENCE: 92
tggacactgg acttcctcc                                                   19

<210> SEQ ID NO 93
<211> LENGTH: 86
<212> TYPE: DNA
<213> ORGANISM: Artificial Sequence
<220> FEATURE:
<223> OTHER INFORMATION: Synthetic sequence from Fig. 4B: 106

<400> SEQUENCE: 93
tggacactgg acttcctccg agagcggctg cttgtctgag accccttagt ccttgtcaca     60
ctttagacta gtggttctca aacttc                                           86

<210> SEQ ID NO 94
<211> LENGTH: 113
<212> TYPE: DNA
<213> ORGANISM: Artificial Sequence
<220> FEATURE:
<223> OTHER INFORMATION: Synthetic sequence from Fig. 4B: 108

<400> SEQUENCE: 94
acactggact tcctccgaga gcggctgctt gtctggatcc aagataagac cagggtggct     60
gggtgagacc ccttagtcct tgtcacactt tagactagtg gttctcaaac ttc            113
```

METHODS AND COMPOSITIONS FOR GENERATION OF BAX-AND BAK-DEFICIENT CELL LINES

CROSS-REFERENCE TO RELATED APPLICATIONS

The present application claims the benefit of U.S. Provisional Application No. 61/131,579, filed Jun. 10, 2008 and U.S. Provisional Application No. 61/133,792, filed Jul. 2, 2008, the disclosures of which are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the fields of genome engineering and generation of cell lines deficient in expression of Bax and/or Bak as well as use of Bax/Bak deficient cells lines for the production of proteins (e.g., antibodies, antigens, etc.), viruses and/or viral vectors.

BACKGROUND

Apoptosis, or programmed cell death, can be triggered by extrinsic or intrinsic signals, as well as developmental cues. Two major apoptotic pathways have been identified: an extrinsic cell death pathway in which apoptosis is initiated through ligand binding to cell surface receptors expressed on the cell that will subsequently die, and an intrinsic cell death pathway in which apoptosis is initiated within the cell.

Tumor necrosis factor receptor family members are among the best characterized of receptors involved in the extrinsic death pathway. Upon the engagement of ligand, these receptors initiate the formation of a death-inducing signaling complex, which includes an essential adaptor molecule FADD. FADD in turn recruits Caspase 8, which in turn is activated through an autoproteolytic process. Once activated, Caspase 8 initiates both the activation of additional caspases such as Caspase 9 and Caspase 3, and the degradation of intracellular substrates, which eventually results in cell death. The TNF receptor family includes TNFR1; Fas; DR3 proteins such as Apo3, WSL-1, TRAMP, and LARD; DR4; DR5 proteins such as TRAIL-R2, TRICK2, and KILLER; and DR6.

Members of the Bcl-2 family of proteins are characterized by their ability to modulate cell death. Bcl-2 and some of its homologues, such as Bcl-xl, inhibit apoptosis, whereas other family members, such as Bax and Bak, induce or accelerate apoptosis under certain conditions. Bak and Bax, as well as Bcl-xs, Bid, Bim, Bad and Bik, constitute the pro-apoptotic group of Bcl-2 proteins.

The Bax protein shares highly conserved domains with Bcl-2, some of which are required for the formation of Bax/Bcl-2 heterodimers, which are thought to be important for the survival or death response to apoptotic signals. Following its activation, Bax translocates to the outer mitochondrial membrane where it oligomerizes, renders the membrane permeable, and releases several death-promoting factors, including cytochrome C (Scorrano et al. (2003) *Biochem. Biophys. Res. Commun.* 304:437-444). Bax can be rendered inactive in normal cells via interaction with the Ku70 protein, which sequesters Bax from mitochondria (Sawada et al. (2003) *Nat. Cell Biol.* 5:320-329).

Bak also promotes cell death and counteracts the protection from apoptosis provided by Bcl-2. Like Bax, the Bak gene product primarily enhances apoptotic cell death following an appropriate stimulus. Bak is a potent inducer of apoptosis in various cell types.

Cell lines in which expression of Bax and/or Bak is reduced by introduction of antisense molecules have been described. See, e.g., Mandic et al. (2001) *Mol. Cell Biol.* 21:3684-3691. In addition, Bax and/or Bak deficient fibroblasts have also been immortalized to create cell lines. See, U.S. Patent Application No. 20030091982. Furthermore, naturally occurring zinc finger proteins (Grimes et al. (1996) *Proc. Nat'l. Acad. Sci. USA* 93:14569-14573) fused to repression domains and engineered zinc finger proteins and nucleases (see, U.S. Patent Publication No. 20060063231) have also been described for the inactivation of Bax and/or Bak. Engineered zinc finger nucleases have also been used to inactivate endogenous dihydrofolate reductase (dhfr) and CCR5 genes. See, e.g., U.S. Patent Publication No. 20080015164 and PCT Publication WO 2007/139982.

However, there remains a need for methods and compositions for inactivation of Bax and Bak, for example to facilitate generation of apoptosis-resistant cell lines.

SUMMARY

Disclosed herein are methods and compositions for partial or complete inactivation of Bax and/or Bak in a target cell, for example to generate Bax and/or Bak deficient or knockout cell lines that are resistant to wide variety of intrinsic death stimuli. These cell lines are advantageously used for recombinant protein (e.g., antibody, antigen, therapeutic protein) production because, unlike conventional cell lines, Bax/Bak-deficient cell lines continue to produce high levels of protein in culture even after many passages.

Bax/Bak deficient cells lines are also useful as producer cell lines for the generation of viral vectors and/or viral vectors expressing gene products e.g. in the generation of recombinant lentiviral, adenoviral or adeno-associated viral (AVV) vectors. Currently, the methods used for generating these viral vectors place significant stress on the host cells leading (in unmodified host cells) to poor vector yields via untimely apoptosis. Thus, the present disclosure addresses the need for apoptosis-resistant Bax/Bac deficient cells lines for the production of viral vectors.

In addition, Bax and/or Bak deficient cell lines are useful for the in vitro production of vaccines such as those targeting human influenza virus. Apoptosis of such vaccine producer cells is a significant source of (i) reduced overall yield, and (ii) or contamination that can result in the failure of a vaccine lot and the inability to use the vaccine lot in humans.

Bax and/or Bak deficient cell lines are also useful for studying agents affecting cancer and other diseases in which apoptosis is implicated (e.g., Alzheimer's, Parkinson's, etc.). Likewise, Bax and/or Bak deficient cell lines provide useful tools for basic research and drug discovery. Such lines provide increased survival of cells in response to certain experimental conditions e.g. nucleic acid delivery procedures such as electroporation, viral transduction, liposome mediated-delivery etc. and/or in response to the delivery of a toxic or stress-inducing payload which can facilitate the measurement of drug-target interactions and basic research knowledge via the study of such interactions in the absence of the apoptotic response.

In one aspect, zinc finger proteins, engineered to bind in a BAX gene, are provided. Any of the zinc finger proteins described herein may include 1, 2, 3, 4, 5, 6 or more zinc fingers, each zinc finger having a recognition helix that binds to a target subsite in a BAX gene. In certain embodiments, the zinc finger proteins comprise 4 fingers (designated F1, F2, F3, F4 and optionally F5) and comprise the amino acid sequence of the recognition helices shown in Table 1.

In one aspect, zinc finger proteins, engineered to bind in a BAK gene, are provided. Any of the zinc finger proteins described herein may include 1, 2, 3, 4, 5, 6 or more zinc fingers, each zinc finger having a recognition helix that binds to a target subsite in a BAK gene. In certain embodiments, the zinc finger proteins comprise 4 or 5 fingers (designated F1, F2, F3, F4 and F5) and comprise the amino acid sequence of the recognition helices shown in Table 2.

In certain embodiments, provided herein is an engineered zinc finger protein DNA-binding domain, wherein the DNA-binding domain comprises four zinc finger recognition regions ordered F1 to F4 from N-terminus to C-terminus, and wherein F1, F2, F3, and F4 comprise the following amino acid sequences: F1: RSDHLST (SEQ ID NO:1); F2: DRSHLAR (SEQ ID NO:2); F3: QSSHLTR (SEQ ID NO:3); and F4: RSDNLRE (SEQ ID NO:4).

In certain embodiments, provided herein is an engineered zinc finger protein DNA-binding domain, wherein the DNA-binding domain comprises four zinc finger recognition regions ordered F1 to F4 from N-terminus to C-terminus, and wherein F1, F2, F3, and F4 comprise the following amino acid sequences: F1: RSANLSV (SEQ ID NO:5); F2: DRANLSR (SEQ ID NO:6); F3: NRTDLIR (SEQ ID NO:7); and F4: TSSNLSR (SEQ ID NO:8).

In other embodiments, the disclosure provides an engineered zinc finger protein DNA-binding domain, wherein the DNA-binding domain comprises five zinc finger recognition regions ordered F1 to F5 from N-terminus to C-terminus, and wherein F1, F2, F3, F4 and F5 comprise the following amino acid sequences: F1: RSDHLTT (SEQ ID NO:9); F2: RSDHLSE (SEQ ID NO:10); F3: RNDNRKT (SEQ ID NO:11); F4: QSGHLQR (SEQ ID NO:12); and F5 QSGHLSR (SEQ ID NO:13).

In other embodiments, the disclosure provides an engineered zinc finger protein DNA-binding domain, wherein the DNA-binding domain comprises four zinc finger recognition regions ordered F1 to F4 from N-terminus to C-terminus, and wherein F1, F2, F3, and F4 comprise the following amino acid sequences: F1: RSDSLSA (SEQ ID NO:14); F2: DRSSRTK (SEQ ID NO:15); F3: RSDDLTR (SEQ ID NO:16); and F4: RSDALAR (SEQ ID NO:17).

In other embodiments, the disclosure provides an engineered zinc finger protein DNA-binding domain, wherein the DNA-binding domain comprises four zinc finger recognition regions ordered F1 to F5 from N-terminus to C-terminus, and wherein F1, F2, F3, F4 and F5 comprise the following amino acid sequences: F1: DRSDLSR (SEQ ID NO:45); F2: NRTDLIR (SEQ ID NO:7); F3: TSSNLSR (SEQ ID NO:8); F4: RSDTLSQ (SEQ ID NO:46); and F5: DRSARTR (SEQ ID NO:47).

In other embodiments, the disclosure provides an engineered zinc finger protein DNA-binding domain, wherein the DNA-binding domain comprises four zinc finger recognition regions ordered F1 to F5 from N-terminus to C-terminus, and wherein F1, F2, F3, F4 and F5 comprise the following amino acid sequences: F1: RSDALSV (SEQ ID NO:48); F2: DSSHRTR (SEQ ID NO:49); F3: QNAHRKT (SEQ ID NO:50); F4: RSDHLST (SEQ ID NO:1); and F5: TSGHLSR (SEQ ID NO:51).

In other embodiments, the disclosure provides an engineered zinc finger protein DNA-binding domain, wherein the DNA-binding domain comprises four zinc finger recognition regions ordered F1 to F5 from N-terminus to C-terminus, and wherein F1, F2, F3, F4 and F5 comprise the following amino acid sequences: F1: QNAHRKT (SEQ ID NO:50); F2: QSGDLTR (SEQ ID NO:53); F3: QSGDLTR (SEQ ID NO:53); F4: QSSNLAR (SEQ ID NO:54); and F5: TSSNRKT (SEQ ID NO:55).

In other embodiments, the disclosure provides an engineered zinc finger protein DNA-binding domain, wherein the DNA-binding domain comprises four zinc finger recognition regions ordered F1 to F6 from N-terminus to C-terminus, and wherein F1, F2, F3, F4 and F5 comprise the following amino acid sequences: F1: RSDNLAR (SEQ ID NO:57); F2: QSGDLTR (SEQ ID NO:53); F3: DNRQLIT (SEQ ID NO:58); F4: TSSNLSR (SEQ ID NO:8); F5: RSDTLSR (SEQ ID NO:59); and F6: RNDDRIT (SEQ ID NO:60).

In other embodiments, the disclosure provides an engineered zinc finger protein DNA-binding domain, wherein the DNA-binding domain comprises four zinc finger recognition regions ordered F1 to F5 from N-terminus to C-terminus, and wherein F1, F2, F3, F4 and F5 comprise the following amino acid sequences: F1: RSDNLTT (SEQ ID NO:62); F2: RSDHLSR (SEQ ID NO:63); F3: QSSDLRR (SEQ ID NO:64); F4: QSSHLTR (SEQ ID NO:3); and F5: RSDHLTQ (SEQ ID NO:65).

In other embodiments, the disclosure provides an engineered zinc finger protein DNA-binding domain, wherein the DNA-binding domain comprises four zinc finger recognition regions ordered F1 to F5 from N-terminus to C-terminus, and wherein F1, F2, F3, F4 and F5 comprise the following amino acid sequences: F1: QSGSLTR (SEQ ID NO:67); F2: TSSNRKT (SEQ ID NO:55); F3: DRSHLTR (SEQ ID NO:68); F4: RSDDRKT (SEQ ID NO:69); F5: NRTDLIR (SEQ ID NO:7) and F6: TSSNLSR (SEQ ID NO:8).

In another aspect, fusion proteins comprising any of the zinc finger proteins described herein and at least one cleavage domain or at least one cleavage half-domain, are also provided. In certain embodiments, the cleavage half-domain is a wild-type FokI cleavage half-domain. In other embodiments, the cleavage half-domain is an engineered FokI cleavage half-domain.

In yet another aspect, a polynucleotide encoding any of the proteins described herein is provided.

In yet another aspect, also provided is an isolated cell comprising any of the proteins and/or polynucleotides described herein. In certain embodiments, cell lines in which Bax and/or Bak are inactivated are generated by culturing of cells comprising any of the proteins and/or polynucleotides described herein to generate Bax and/or Bak deficient cell lines. In certain embodiments, Bax or Bak are inactivated (partially or fully) in the cell or cell line.

In addition, methods of using the zinc finger proteins and fusions thereof in methods of inactivating Bax and/or Bak in a cell or cell line are provided. In certain embodiments, inactivating Bax and/or Bak in a cell produces a cell line in which Bax and/or Bak remain inactivated following passage of the cells, thereby creating a cell line which is resistant to apoptosis.

Thus, in another aspect, provided herein is a method for inactivating a cellular BAX and/or BAK gene (e.g., an endogenous BAK/BAX gene(s)) in a cell, the method comprising: (a) introducing, into a cell, a first nucleic acid encoding a first polypeptide, wherein the first polypeptide comprises: (i) a zinc finger DNA-binding domain that is engineered to bind to a first target site in an endogenous BAK and/or BAX gene;

and (ii) a cleavage domain; such that the polypeptide is expressed in the cell, whereby the polypeptide binds to the target site and cleaves the BAK and/or BAX gene. In certain embodiments, the methods further comprise introducing a nucleic acid encoding a second polypeptide, wherein the second polypeptide comprises: (i) a zinc finger DNA-binding domain that is engineered to bind to a second target site in the BAK and/or BAX gene; and (ii) a cleavage domain; such that the second polypeptide is expressed in the cell, whereby the first and second polypeptides bind to their respective target sites and cleave the BAK and/or BAX gene. The first and second polypeptides may be encoded by the first nucleic acid or by different nucleic acids. In certain embodiments, one or more additional polynucleotides or polypeptides are introduced into the cells, for example polynucleotides encoding additional zinc finger proteins.

In another aspect, provided herein is a method for producing a cell line that is deficient in Bak and/or Bax expression (i.e. expression of Bak and/or Bax is reduced or eliminated). In certain embodiments, the methods involve partial or complete inactivation of Bak and/or Bax by introduction of one or more engineered zinc finger nucleases (or nucleic acids encoding engineered nucleases) and subsequent culturing of the cells to generate a cell line that is deficient with respect to Bax and/or Bak.

In yet another aspect, the disclosure provides a method of producing a protein or virus or viral vector of interest in a host cell or cell line in which Bak and/or Bax have been inactivated. In certain embodiments, the method comprises the steps of: (a) providing a host cell comprising an endogenous BAX and/or BAK gene; (b) inactivating the endogenous BAX and/or BAK gene of the host cell by any of the methods described herein; and (c) introducing an expression vector comprising a transgene, the transgene comprising a sequence encoding a protein, virus or viral vector of interest into the host cell, thereby producing the protein, virus or viral vector of interest. In other embodiments, the method comprises the steps of: providing a Bak- and/or Bax-deficient cell line; introducing, into the cell line, a polynucleotide encoding at least one recombinant protein of interest, virus, or viral vector under conditions such that the recombinant protein is expressed in the cell line. The polynucleotide encoding the protein, virus, or viral vector of interest may be stably and/or transiently introduced into the Bak- and/or Bax-deficient cell line. In any of the methods described herein, the protein of interest comprises an antibody, e.g., a monoclonal antibody. In other embodiments, the protein of interest comprises a protein useful as an antigen as a vaccine, e.g., the HA protein derived from the influenza virus. In further embodiments, the methods are used to produce whole virus vaccines. In still other embodiments, a recombinant viral vector is produced by the above methods, for example by a method comprising the steps of: (a) providing a host cell comprising an endogenous BAX and/or BAK gene; (b) inactivating the endogenous BAX and/or BAK gene of the host cell by any of the methods described herein; and (c) introducing one or more expression vectors comprising a recombinant viral vector system, thereby producing the recombinant viral vector of interest.

In any of the cell, cell lines and methods described herein, the cell or cell line can be a COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), PerC.6® (Crucell); EBx™ (Sigma-Aldrich Group), insect cells such as Spodoptera fugiperda (Sf), or fungal cells such as Saccharomyces, Pichia and Schizosaccharomyces or other cell lines known in the art or developed de novo.

These and other aspects will be readily apparent to the skilled artisan in light of disclosure as a whole.

BRIEF DESCRIPTION OF THE DRAWINGS

FIG. 1 (SEQ ID NOS: 75-79) depicts genotyping of CHO-K1 cells in which exon 2 of the BAK gene was knocked out using engineered zinc finger nucleases. Deleted bases (as compared to wild-type) are shown by colons. The top line (39F/38R) is the wild-type sequence and shows the start codon boxed. Clone 8H6 is a compound heterozygote knock-out (KO) in which allele A shows a different base pair deletion pattern than allele B. Clone 8D4 is a homozygous knockout. SEQ ID NO:75 shows sequence of 39F\38R; SEQ ID NO:76 shows sequence of Bak 8H6-1 and Bak 8H6-3; SEQ ID NO:77 shows sequence of Bak 8H6-2 and Bak 8H6-4; SEQ ID NO:78 shows sequence of Bak 8D4-1; and SEQ ID NO:79 shows sequence of Bak 8D4-2, Bak 8D4-3 and Bak8D4-4.

FIG. 2, panels A to D, depict modification of BAK and BAX genes in MDCK cells by ZFNs. FIG. 2A is a gel showing PCR products resulting from cleavage events in a CEL-I assay in the BAK-targeted ZFN-treated cell pool (17623/17622 or 17627/17626) and non-ZFN-treated cells ("vector only"). The percentage of alleles modified by ZFNs at the BAK locus is shown beneath the two left-most lanes. FIG. 2B is a gel showing PCR products resulting from cleavage events in a CEL-I assay in the BAX-targeted ZFN-treated cell pool (17658/17659) and non-ZFN-treated cells ("vector only"). The percentage of alleles modified by ZFNs at the BAX locus is shown beneath the right-most lane (8%). FIG. 2C shows PCR results of various MDCK clones treated with BAK-targeted ZFNs. The clone number is indicated on the top of each lane and the mutations at each BAK allele shown below the gel. FIG. 2D shows a summary of PCR analysis of MDCK cells treated with BAX-specific ZFNs. As can be seen from the figure, BAX single knockouts were obtained with a deletion of 30 bp on one allele and an insertion of 1 bp on the other. For the BAX/BAK double knockouts, BAX alleles were targeted in Bak-deficient clones using BAX-specific ZFNs. As can be seen, several heterozygous clones were identified which contained one wild type BAX allele, and one mutated BAX allele.

FIG. 3 depicts RNA analysis in Bak knockout cells. Lanes 1 to 5 of the gel depicted show RT-PCR products of Bak transcripts from exons 1-4 from the indicated clones and controls. Lanes 6-10 show RT-PCR products of Bax transcripts from exons 4-6 in the same clones and controls. As shown by the arrow in lane 4, most of the transcripts formed from clone 8H6 (the compound heterozygote clone) skip exon 2.

FIG. 4, panels A and B, depict analysis of PCR products of 21 positive Bak/Bax double knockout clones generated on the background of the Bak 8H6 knock-out. Clone number is indicated above each lane. Of the 79 clones analyzed, 21 (27%) were digested with Bsl I, indicative of mutation at the site of ZFN cleavage. The sequence of the Bsl I-resistant alleles in FIG. 4A is shown in FIG. 4B (SEQ ID NOS: 80-94). The top line (52F/114R) is the wild-type sequence with a 4 bp gap inserted to facilitate alignment. Insertions and deletions for clones designated 30, 35, 45, 71 and 97 were large and, accordingly, are not depicted. The genotype of clone #100 was not determined. SEQ ID NO:80 shows sequence of 52F114R; SEQ ID NO:81 shows sequence of the clones designed 11, 18, 22, 28, 50 and 91; SEQ ID NO:82 shows sequence of the clone designated 13; SEQ ID NO:83 shows sequence of the clone designated 30; SEQ ID NO:84 shows sequence of the clone designated 35; SEQ ID NO:85 shows sequence of the clones designated 40 and 87; SEQ ID NO:86 shows sequence of the clone designated 46; SEQ ID NO:87 shows sequence of the clone designated 47; SEQ ID NO:88 shows sequence of the clone designated 57; SEQ ID NO:89 shows sequence of the clone designated 71; SEQ ID NO:90 shows sequence of the clone designated 72; SEQ ID NO:91 shows sequence of the clone designated 93; SEQ ID NO:92 shows sequence of the clone designated 97; SEQ ID NO:93 shows sequence of the clone designated 106; and SEQ ID NO:94 shows sequence of the clone designated 108.

FIG. 5 depicts Bax and Bak protein expression in Bax/Bak double knockout cells. The clone number is indicated above each line and the antibody used for detection is indicated below each gel (Abcam #7977 for Bax protein and Sigma B5877 for Bak protein). As shown, the double KO cells do not produce full-length or truncated Bax and Bak proteins.

FIG. 6 is a graph depicting apoptosis in Bax/Bak double KO cells as measured by caspase activity (Homogenous Caspases Assay, Roche Diagnostics Corporation), which is indicative of apoptosis. The white bar shows caspase activity after induction with 1 uM staurosporine; the gray bar shows uninduced cells. The Bax-Bak-/- clones tested were: clone 47 (bars second from the left); clone 71 (bars second from the right); and clone 91 (right-most bars).

FIG. 7 is a graph depicting protein (monoclonal antibody) production in BAX and/or BAK knockout cell clones. Diamonds show antibody production in wild-type CHO cells and squares depict show protein production in clone 8H6-71 BAX⁻BAK⁻/⁻ CHO cells.

DETAILED DESCRIPTION

Described herein are compositions and methods for partial or complete inactivation of a BAK gene and/or a BAX gene. Also disclosed are methods of making and using these compositions (reagents), for example to inactivate one or both of Bak and Bax in a target cell. Inactivation of Bak and/or Bax in a target cell can be used to generate cell lines that are resistant to apoptosis and useful in producing recombinant proteins such as antibodies, recombinant viral vectors and in the manufacture of vaccines (e.g., one or more antigenic proteins, whole virus vaccines, etc.).

In mammalian cells, Bax and Bak have been shown to be involved in promoting programmed cell death. See, Zhang et al. (2000) Science 290:989-992. Thus, the methods and compositions described herein provide a highly efficient method for targeted gene knockout (partial or complete) of Bax and/or Bak that allows for the generation of Bax and/or Bak deficient cells lines. Bax/Bak-deficient cell lines can be cultured in vitro for prolonged periods without undergoing aberrant growth characteristics seen in many immortalized cell lines. Thus, the cell lines described herein are useful in producing recombinant proteins (e.g., antibodies), vaccines or recombinant viral vectors and in studying apoptosis-related diseases and conditions.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Therefore, engineered zinc finger proteins are proteins that are non-naturally occurring in that they contain non-naturally occurring recognition helix regions. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. patent application Ser. Nos. 10/912,932 and 11/304,981 and U.S. Provisional Application No. 60/808,486 (filed May 25, 2006), incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequenced may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Gene inactivation refers to any reduction in gene expression as compared to a cell that does not include a ZFP as described herein. Thus, gene inactivation may be partial or complete.

"Eukaryotic" cells include, but are not limited to, fungal cells (such as yeast), plant cells, animal cells, mammalian cells and human cells (e.g., T-cells).

A "cell line" refers to a population of cells established in tissue culture from a primary culture. Thus, cell lines generated using zinc finger nucleases arise from a cell (or cell line) in which one or more target genes (e.g., BAK and/or BAX) have been partially or completely inactivated by one or more zinc finger nucleases and in which the progeny of the cell (or cell line) retain the partial or complete inactivation phenotype after multiple passages in culture. Furthermore, a cell or cell line is "deficient" in expression of one or more indicated genes when expression of the gene(s) is(are) reduced or eliminated (knockouts). Thus, a Bax/Bak-deficient cell lines show reduced or knocked-out expression of Bax and Bak.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

The term "antibody" as used herein includes antibodies obtained from both polyclonal and monoclonal preparations, as well as, the following: hybrid (chimeric) antibody molecules (see, for example, Winter et al., Nature (1991) 349: 293-299; and U.S. Pat. No. 4,816,567); F(ab')2 and F(ab) fragments; Fv molecules (non-covalent heterodimers, see, for example, Inbar et al., Proc Natl Acad Sci USA (1972) 69:2659-2662; and Ehrlich et al., Biochem (1980) 19:4091-4096); single-chain Fv molecules (sFv) (see, for example, Huston et al., Proc Natl Acad Sci USA (1988) 85:5879-5883); dimeric and trimeric antibody fragment constructs; minibodies (see, e.g., Pack et al., Biochem (1992) 31:1579-1584; Cumber et al., J Immunology (1992) 149B: 120-126); humanized antibody molecules (see, for example, Riechmann et al., Nature (1988) 332:323-327; Verhoeyan et al., Science (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

By vaccine is meant an agent used to stimulate the immune system of a living-organism so that protection against future harm is provided. Immunization refers to the process of inducing an antibody and/or cellular immune response in which T-lymphocytes can either kill the pathogen and/or activate other cells (e.g., phagocytes) to do so in an organism, which is directed against a pathogen or antigen to which the organism has been previously exposed. The term "immune response," as used herein, encompasses, for example, mechanisms by which a multi-cellular organism produces antibodies against an antigenic material which invades the cells of the organism or the extra-cellular fluid of the organism. The antibody so produced may belong to any of the immunological classes, such as immunoglobulins A, D, E, G or M. Other types of responses, for example cellular and humoral immunity, are also included. Immune response to antigens is well studied and widely reported. A survey of immunology is given e.g., in Roitt I., (1994). Essential Immunology, Blackwell Scientific Publications, London. Methods in immunology are routine and conventional (see, e.g., in Current Protocols in Immunology; Edited by John E. Coligan et al., John Wiley & Sons, Inc.).

A "recombinant viral vector" refers to a recombinant polynucleotide vector comprising one or more heterologous sequences (i.e., polynucleotide sequence not of viral origin). In the case of recombinant parvovirus vectors, the recombinant polynucleotide is flanked by at least one, preferably two, inverted terminal repeat sequences (ITRs).

A "recombinant AAV vector (rAAV vector)" refers to a polynucleotide vector comprising one or more heterologous sequences (i.e., polynucleotide sequence not of AAV origin) that are flanked by at least one, preferably two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV Vector is incorporated into a larger polynucleotide (e.g. in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV can be in any of a number of forms, including, but not limited to, plasmids, linear artificial chromosomes, complexed with lips, encapsulated within liposomes, and, most preferable, encapsidated in a viral particle, particularly AAV. An rAAV vector can be packaged into an AAV virus particle to generate a "recombinant adeno-associated virus" (rAAV). The maximum size vector that can be packaged to yield an infectious viral particle is approximately 5.2 kb.

Zinc Finger Nucleases

Described herein are zinc finger nucleases (ZFNs) that can be used for inactivation of a BAK and/or BAX gene. ZFNs comprise a zinc finger protein (ZFP) and a nuclease (cleavage) domain.

A. Zinc Finger Proteins

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length (e.g., TGEKP (SEQ ID NO:18), TGGQRP (SEQ ID NO:74), TGQKP (SEQ ID NO:19), and/or TGSQKP (SEQ ID NO:20)). See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Tables 1 and 2 describe zinc finger binding domains that have been engineered to bind to nucleotide sequences in a BAX gene (Table 1) and a BAK gene (Table 2). Each row describes a separate zinc finger DNA-binding domain. The DNA target sequence for each domain is shown in the first column and the second through fifth columns show the amino acid sequence of the recognition region (amino acids −1 through +6, with respect to the start of the helix) of each of the zinc fingers (F1 through F4 or F5) in the protein. Also provided in the first column is an identification number for the proteins.

TABLE 1

ZINC FINGER NUCLEASES TARGETED TO BAX

| ZFN name Target sequence | F1 | F2 | F3 | F4 | F5 |
|---|---|---|---|---|---|
| SBS 10077 CAGGGTGGCTGG (SEQ ID NO: 21) | RSDHLST (SEQ ID NO: 1) | DRSHLAR (SEQ ID NO: 2) | QSSHLTR (SEQ ID NO: 3) | RSDNLRE (SEQ ID NO: 4) | N/A |
| SBS 10079 GATCCAGACAAG (SEQ ID NO: 22) | RSANLSV (SEQ ID NO: 5) | DRANLSR (SEQ ID NO: 6) | NRTDLIR (SEQ ID NO: 7) | TSSNLSR (SEQ ID NO: 8) | N/A |
| SBS 17658 GTCCTGGATCCAGCC (SEQ ID NO: 43) | DRSDLSR (SEQ ID NO: 45) | NRTDLIR (SEQ ID NO: 7) | TSSNLSR (SEQ ID NO: 8) | RSDTLSQ (SEQ ID NO: 46) | DRSARTR (SEQ ID NO: 47) |
| SBS 17659 GGTTGGgTGAGGCCTG (SEQ ID NO: 44) | RSDALSV (SEQ ID NO: 48) | DSSHRTR (SEQ ID NO: 49) | QNAHRKT (SEQ ID NO: 50) | RSDHLST (SEQ ID NO: 1) | TSGHLSR (SEQ ID NO: 51) |

TABLE 2

Zinc finger nucleases targeted to BAK

| ZFN name Target sequence | F1 | F2 | F3 | F4 | F5 | F6 |
|---|---|---|---|---|---|---|
| SBS 11205 GGAGGAAAGGGG TGG (SEQ ID NO: 23) | RSDHLTT (SEQ ID NO: 9) | RSDHLSE (SEQ ID NO: 10) | RNDNRKT (SEQ ID NO: 11) | QSGHLQR (SEQ ID NO: 12) | QSGHLSR SEQ ID NO: 13) | N/A |
| SBS 10350 GTGGCGGCCCTG (SEQ ID NO: 24) | RSDSLSA (SEQ ID NO: 14) | DRSSRTK (SEQ ID NO: 15) | RSDDLTR (SEQ ID NO: 16) | RSDALAR (SEQ ID NO: 17) | N/A | N/A |
| SBS 14238 TTTCAGGCCTTGG TTGGC (SEQ ID NO: 33) | DRSHLSR (SEQ ID NO:34) | TSGSLTR (SEQ ID NO: 35) | RSDSLSA (SEQ ID NO: 14) | DRSSRTK (SEQ ID NO: 15) | RSDNLSE SEQ ID NO: 36) | HSNAR KT (SEQ ID NO: 37) |
| SBS 10526 CGTCTGGACAAG (SEQ ID NO: 38) | RSDNLSV (SEQ ID NO: 39) | DRSNLTR (SEQ ID NO: 40) | RSDTLSE (SEQ ID NO: 41) | RSQTRKT (SEQ ID NO: 42) | N/A | N/A |
| SBS 17622 AATGATGCAGCAT GA (SEQ ID NO: 52) | QNAHRKT (SEQ ID NO: 50) | QSGDLTR (SEQ ID NO: 53) | QSGDLTR (SEQ ID NO: 53) | QSSNLAR (SEQ ID NO: 54) | TSSNRKT (SEQ ID NO: 55) | N/A |
| SBS 17623 CCGGTGGATCGC GCAGAG (SEQ ID NO: 56) | RSDNLAR (SEQ ID NO: 57) | QSGDLTR (SEQ ID NO: 53) | DNRQLIT (SEQ ID NO: 58) | TSSNLSR (SEQ ID NO: 8) | RSDTLSR (SEQ ID NO: 59) | RNDD RIT (SEQ ID NO: 60) |

TABLE 2-continued

Zinc finger nucleases targeted to BAK

| ZFN name Target sequence | F1 | F2 | F3 | F4 | F5 | F6 |
|---|---|---|---|---|---|---|
| SBS 17627 AGGGGTgGCTGG GTAG (SEQ ID NO: 61) | RSDNLTT (SEQ ID NO: 62) | RSDHLSR (SEQ ID NO: 63) | QSSDLRR (SEQ ID NO: 64) | QSSHLTR (SEQ ID NO: 3) | RSDHLTQ (SEQ ID NO: 65) | N/A |
| SBS 17626 GATCCACCGGGCA ATGCA (SEQ ID NO: 66) | QSGSLTR (SEQ ID NO: 67) | TSSNRKT (SEQ ID NO: 55) | DRSHLTR (SEQ ID NO: 68) | RSDDRKT (SEQ ID NO: 69) | NRTDLIR (SEQ ID NO: 7) | TSSNLSR (SEQ ID NO: 8) |

As described below, in certain embodiments, a four- or five-finger binding domain as shown in Tables 1 and 2 is fused to a cleavage half-domain, such as, for example, the cleavage domain of a Type IIs restriction endonuclease such as FokI. One or more pairs of such zinc finger/nuclease half-domain fusions are used for targeted cleavage, as disclosed, for example, in U.S. Patent Publication No. 20050064474.

For targeted cleavage, the near edges of the binding sites can separated by 5 or more nucleotide pairs, and each of the fusion proteins can bind to an opposite strand of the DNA target. Typically, the ZFNs shown in Tables 1 and 2 are used in pairs for cleavage of their target gene. Following the present disclosure, ZFNs can be targeted to any sequence in a BAX or BAK gene.

B. Cleavage Domains

The ZFNs also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and in U.S. application Ser. No. 11/805,850 (filed May 23, 2007), the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of U.S. Provisional Application No. 60/808,486 (filed May 25, 2006), the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication No. 20050064474 (see, e.g., Example 5); and WO 07/139898.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

C. Additional Methods for Targeted Cleavage

Any nuclease having a target site in a BAX or BAK gene can be used in the methods disclosed herein. For example, homing endonucleases and meganucleases have very long recognition sequences, some of which are likely to be present, on a statistical basis, once in a human-sized genome. Any such nuclease having a unique target site in a BAX and/or BAK gene can be used instead of, or in addition to, a zinc finger nuclease, for targeted cleavage in these genes.

Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66.

Delivery

The ZFNs described herein may be delivered to a target cell by any suitable means. Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line.

Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more of the ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more ZFN encoding sequences. Thus, when one or more pairs of ZFNs are introduced into the cell, the ZFNs may be carried on the same vector or on different vectors. When multiple vectors are used, each vector may comprise a sequence encoding one or multiple ZFNs.

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids encoding engineered ZFPs include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol* 65:2220-2224 (1991); PCT/US94/05700).

In applications in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998); Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces*. Progeny, variants and derivatives of these cell lines can also be used.

Kits

Also provided are kits comprising any of the compositions described herein or for practicing any of the methods described herein. The kits typically contain one or more zinc finger proteins (e.g., zinc finger nucleases) that bind to a target site in Bak or Bax. Thus, kits for generating BAK and/or BAX knockout cell lines are provided. The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

Applications

The disclosed methods and compositions can be used for inactivation of a BAX and/or BAK genomic sequence. As noted above, inactivation includes partial or complete repression of Bax and/or Bak gene expression in a cell. Bax- and/or Bak-deficient cells lines (e.g., double Bax/Bak knockout cell lines) can also be generated as described herein. Inactivation of Bak and/or Bax can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, targeted recombination of an exogenous nucleic acid sequence encoding a sequence of interest, so as to disrupt the gene or regulatory region, or by targeting recombination of a splice acceptor sequence into an intron to cause mis-splicing of the transcript.

There are a variety of applications for ZFN-mediated inactivation (knockout) of Bax and or Bak. For example, cell lines deficient in Bax and/or Bak generated as described herein are resistant to apoptosis and grow and remain healthy longer when expressing exogenous proteins of interest in culture than cell lines that are not deficient in Bax and/or Bak. Accordingly, Bax/Bak deficient cell lines as described herein can be used for prolonged and efficient production of one or more proteins of interest (e.g., antibodies, antigens, therapeutic proteins) and/or recombinant viral vectors (e.g. Lentiviral, Adenoviral or Adeno-Associated Viral (AAV) vectors. In addition, disruption of other apoptosis-related genes may prove to be effective at preventing apoptosis, either singly or in combination. In particular, members of the BH3-only family of apoptosis-promoting proteins (i.e. Bik, Bim, Bad etc.) may be targets for gene disruption and/or knockout.

In addition, the Bax and/or Bak deficient cell lines described herein are useful for production of whole virus and/or subunit vaccines. It is known that, for example, influenza virus infected cell lines show marked evidence of apoptosis. Thus, use of the Bax and/or Bak deficient cell lines of the instant invention can be used for more efficient and prolonged production of viral vaccines such as influenza vaccines. Production of influenza vaccines in cells from species not susceptible to influenza infection is especially desirable, for example, in dog cells such as MDCK cells. It is also known that host cell apoptosis results in the potential for contamination of the vaccine product with components of the production cell. Such contamination can result in the failure of a product lot to achieve the necessary purity and quality for release and use in humans. A reduction in contaminants via the prevention of apoptosis obtain by using the Bax and/or Bak deficient cell lines may lead to both yield and efficiency gains.

EXAMPLES

Example 1

Design and Construction of BAX- and BAK-ZFNs

Zinc finger proteins were designed to recognize target sites in BAX and BAK. Exemplary designs are shown in Tables 1 and 2.

Plasmids comprising sequences encoding the appropriate pair of ZFNs were constructed essentially as described in Urnov et al. (2005) *Nature* 435(7042):646-651. See, also, U.S. Patent Publication No. 20080015164 and WO 2007/139982.

Example 2

Genotypic Analysis

BAK- and BAX-inactivated clones in various cell types were generated and analyzed at the genetic level.

A. CHO Cells

A plasmid encoding ZFNs 11205 and 10350 was transfected into CHO K1 cells. CHO K1 cells were obtained from the American Type Culture Collection and grown as recommended in F-12 medium (Invitrogen) supplemented with 10% qualified fetal calf serum (FCS, Cyclone). Cells were disassociated from plastic ware using TrypLE Select™ protease (Invitrogen). For transfection, one million CHO K1 cells were mixed with 2 μg of the zinc-finger nuclease plasmid and 100 μL Amaxa Solution T. Cells were transfected in an Amaxa Nucleofector II™ using program U-23 and recovered into 1.4 mL warm F-12 medium+10% FCS.

Genomic DNA was harvested and a portion of the BAK locus PCR amplified using the oligos GJC 39F (5'-tcaagaggtttcatggcgag-3') (SEQ ID NO:25) and GJC 38R (5'-ttctctctcttgtgcttatgg-3') (SEQ ID NO:26). PCR using the Accuprime HiFi polymerase from InVitrogen was as follows: after an initial 3 minute denaturation at 94° C., 30 cycles of PCR were performed with a 30 second denaturation step at 94° C. followed by a 30 second annealing step at 58° C. followed by a 30 second extension step at 68° C. After the completion of 30 cycles, the reaction was incubated at 68° C. for 7 minutes, then at 10° C. indefinitely.

The PCR products were gel purified and were sequenced and two alleles were recovered. Partial BAK genotypes (deletions) of two exemplary clones are shown in FIG. 1. In both clones, the ZFNs introduced a deletion that included the wild-type start site. Alleles are designated as A and B.

For both clones sequenced, both alleles of BAK were modified. Clone 8H-6 was compound heterozygous (allele A having a larger deletion than allele B) and clone 8D-4 was homozygous. See, FIG. 1.

B. MDCK Cells

BAK- and BAX-targeted ZFNs were also tested in Madin-Darby Canine Kidney (MDCK) cells as described above for CHO cells, except using ZFNs 17622 and 17623 for BAK (which recognize target sites in a dog BAK gene) and ZFNs 17658 and 17659 for BAX (which recognize target sites in a dog BAX gene).

The MDCK BAK- and BAX-ZFN treated cells were also examined by the Surveyor™ nuclease (Transgenomic) as described, for example, in U.S. Patent Publication Nos. 20080015164; 20080131962 and 20080159996. MDCK cells treated with ZFNs 17622/17623 and ZFNs 17627/17626 showed 3.7% and 1.1% disruption, respectively, in the BAK allele (FIG. 2A). MDCK cells treated with ZFNs 17658 and 17659 showed 8.0% disruption in the BAX allele (FIG. 2B).

Genomic DNA was harvested and a portion of the BAK locus PCR amplified using the oligos YS 13F (5'-ctcctttcacagagatgcag-3') (SEQ ID NO:70) and YS 14R (5'-caggagagacagagtggtca-3') (SEQ ID NO:71). Genomic DNA was harvested and a portion of the BAX locus PCR amplified using the oligos YS 21F (5'-aaaaagactgcagtggcgca-3') (SEQ ID NO:72) and YS 22R (5'-tcacccagaggtcaatggat-3') (SEQ ID NO:73). PCR amplicons for BAK and BAX (in both wild-type and BAK-deleted clones) were cloned and sequenced.

As shown in FIG. 2C, analysis of various BAK-specific ZFN-treated clones showed that the ZFN-treated MDCK clones had a disruption in one or both BAK alleles. Similarly, FIG. 2D shows PCR analysis of MDCK cells treated with BAX-specific ZFNs and shows BAX single knockouts were obtained with a deletion of 30 bp on one allele and an insertion of 1 bp on the other. For the BAX/BAK double knockouts, BAX alleles were targeted in Bak-deficient clones using BAX-specific ZFNs. As can be seen, several heterozygous clones were identified which contained one wild type BAX allele, and one mutated BAX allele.

Example 3

RNA Analysis of Bak Deletion Clones

Transcripts of BAK from BAK-inactivated CHO cell clones as described in Example 2 were also analyzed.

RNA was purified from wild-type CHO-K1 cells and both BAK deletion clones using the High Pure RNA Isolation Kit (Roche Applied Science) according to the manufacture's recommendations. Two-and-a-half micrograms of total RNA was used in a reverse transcription reaction as follows: 500 ng oligo(dT) was mixed with the RNA, and 1 µL of a 10 mM dNTP mix. Water was added to a final volume of 20 µL. The mixture was heated to 65° C., chilled on ice, and supplemented with 4 µL 5× First-strand buffer (Invitrogen) and 01.M DTT. The mixture was incubated at 42° C. for 2 minutes. One microliter of Superscript II reverse transcriptase® (InVitrogen) was added to the reaction, and the reaction was then incubated at 42° C. for 50 minutes. The reverse transcription reaction was then halted by incubation at 70° C. for 15 minutes. One microliter of the resulting cDNA was used in a PCR reaction using the Accuprime™ HiFi polymerase from InVitrogen as follows: after an initial 3 minute denaturation at 94° C., 25 cycles of PCR were performed with a 30 second denaturation step at 94° C. followed by a 30 second annealing step at 60° C. followed by a 30 second extension step at 68° C. After the completion of 30 cycles, the reaction was incubated at 68° C. for 7 minutes, then at 10° C. indefinitely. Oligonucleotides for BAK were GJC 24F (5'-catctcacatctggacca-cagccg-3') (SEQ ID NO:27) and GJC 25R (5'-ctggaactctgt-gtcgtatctccgg-3') (SEQ ID NO:28); oligonucleotides for BAX were GJC 12F (5'-cttcttccgggtggcagctg-3') (SEQ ID NO:29) and GJC 23R (5'-cccgaagtatgagaggaggccatc-3') (SEQ ID NO:30).

As shown in FIG. 3, the transcript formed from clone 8H6 (the compound heterozygote clone), shows that this clone skips exon 2. In addition, as expected, deletion of BAK had no effect on the splicing of BAX.

Example 4

Generation and Analysis of BAK/BAX Double Knockout Cell Lines

Cell lines were also created in which both BAK and BAX were inactivated. In particular, zinc finger nucleases directed to BAX were designed and constructed as described above. Plasmids encoding the BAX designs shown in Table 1 into Bak-deficient CHO cells as described in Example 2 and 3.

The cells were tested for BAX inactivation by digestion of BAX PCR products with Bsl I, which detects mutation at the site of ZFN cutting. Approximately 25,000 cells from each clone were lysed in 100 µL QuickExtract™ solution (Epicentre) and one microliter of the resulting crude lysate was used in a PCR reaction using the Accuprime™ HiFi polymerase from Invitrogen as follows: after an initial 3 minute denaturation at 94° C., 35 cycles of PCR were performed with a 30 second denaturation step at 94° C. followed by a 30 second annealing step at 60° C. followed by a 30 second extension step at 68° C. After the completion of 30 cycles, the reaction was incubated at 68° C. for 7 minutes, then at 10° C. indefinitely. Oligonucleotides for screening BAX disruption clones were GJC 52F (5'-cagaggaatgaaagcaaagg-3') (SEQ ID NO:31) and GJC 114R (5'-tgaaccaggctgggagattt-3') (SEQ ID NO:32). One-tenth of a microliter of Bsl I (New England Biolabs) along with 0.1 µL 10 mg/mL BSA and 0.1 µL 10× Buffer #4 (New England Biolabs) was added to the PCR reaction. Digestion was allowed to proceed for 3 hours at 55° C. after which the digestion products were analyzed by 1% agarose gel electrophoresis.

As shown in FIG. 4, 21 of 79 of the $BAK^{-/-}$ BAX-transfected clones contained the predicted disruption of BAX.

The BAK/BAX double knockout clones were also tested for expression of Bax and Bak proteins. Lysates from one million $BAX/BAK^{-/-}$ cells were prepared by resuspension in 100 µL RIPA buffer (Sigma) plus protease inhibitors (Complete Mini tablets, Roche Applied Science) and incubation on ice for 1 hour. Lysates were centrifuged at 14,000 rpm for 10 minutes and 10 µL of the supernatant was used for a Western blot. Protein extracts from the clones were probed with anti-Bax antibody (Abcam and anti-Bak antibody (Sigma). As shown in FIG. 5, $BAX/BAK^{-/-}$ double knockout cells did not express full-length or truncated versions of Bax or Bak proteins.

Example 5

Apoptosis is Prevented in $BAX/BAK^{-/-}$ Double Knockout Cell Lines

The $BAX^-/BAK^{-/-}$ double knockout cell lines were also tested for their resistance to staurosporine-induced apoptosis.

Briefly, 25000 cells from three different $BAX^-/BAK^{-/-}$-knock-out cell lines (#47, 71 and 97) and 25000 wild-type CHO-K1 cells were seeded into a 96-well dish in F-12 medium+10% fetal bovine serum. After 12 hours of growth, the cells were exposed to 1 µM staurosporine (Sigma, S-4400) for 6 hours at 37° C. Activation of caspase (proteases that are only active during apoptosis and are activated by Bak- and Bax-mediated release of cytochrome C from the mitochondrion) was measured with the Homogenous Caspase Assay Kit (Roche Applied Science) according to the manufacturer's instructions. Data were recorded 2.5 hours after the start of the assay. To correct for minor variation in cell seeding density, caspase activity was normalized by LDH-A enzyme activity (a proxy for cell number) using the CytoTox-One™ kit (Promega).

As shown in FIG. 6, apoptosis was not detected in $BAX^-/BAK^{-/-}$ cell lines.

These results show the rapid generation of apoptosis-resistant Bax- and Bak-deficient cell lines using engineered nucleases. Illicit DNA repair through the error-prone process of NHEJ at the site of cleavage resulted in functionally deleterious mutations. Although NHEJ-derived mutations are sometimes small relative to those made by conventional gene disruption, the ability of engineered nucleases (ZFNs) to target these mutations to selected critical regions of BAK and BAX ensured that even small, in-frame deletions would result in inactivation.

Furthermore, although many different subtypes of CHO cell lines exist, often with custom-made genetic or phenotypic changes, the ZFNs described herein can be used to rapidly disrupt BAX and/or BAK in any cell line or subtype. In addition, because zinc finger protein binding sites can be selected that are conserved between mammalian species, ZFNs can be designed to inactivate BAX and BAK in cells lines derived from any species.

Example 6

Production of a Recombinant Protein is Increased in BAX$^-$/BAK$^{-/-}$ Double Knockout Cell Lines Protein production from wild-type CHO-K1 cells and the BAX$^-$BAK$^{-/-}$ clone 8H6-71 (see, FIG. 5) was assayed. Both wild-type and knockout cell lines were transfected with a plasmid containing IgG heavy and light chain genes and a gene for puromycin-resistance. Cells were selected with 8 µg/mL puromycin and the culture supernatant of the puromycin-resistant pool was sampled at two day intervals for 2.5 weeks. The cells were not fed in this experiment, allowing for nutrient starvation and toxic metabolite accumulation to induce apoptosis late in the cultures' growth.

IgG levels were similar in both cultures at days 4-8. From days 12-17 however, IgG levels in the double-knockout culture were 2- to 5-fold higher than in wild-type CHO cell culture (FIG. 7).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A protein comprising an engineered zinc finger protein DNA-binding domain that specifically binds to a target site in a Bak or Bax gene, wherein the DNA-binding domain comprises four, five or six zinc finger recognition regions, ordered F1 to F4 for proteins with four zinc finger domains, ordered F1 to F5 for proteins with five zinc finger domains and ordered F1 to F6 for proteins with six zinc finger domains from N-terminus to C-terminus, and further wherein the zinc finger proteins is selected from the group consisting of a protein comprising the following amino acid sequences in the zinc finger recognition regions:

(i) F1: RSDHLTT (SEQ ID NO:9);
F2: RSDHLSE (SEQ ID NO:10);
F3: RNDNRKT (SEQ ID NO:11);
F4: QSGHLQR (SEQ ID NO:12); and
F5: QSGHLSR (SEQ ID NO:13) and wherein the protein binds to the target sequence shown in SEQ ID NO:23;

(ii) F1: RSDSLSA (SEQ ID NO:14);
F2: DRSSRTK (SEQ ID NO:15);
F3: RSDDLTR (SEQ ID NO:16); and
F4: RSDALAR (SEQ ID NO:17) and wherein the protein binds to the target sequence shown in SEQ ID NO:24;

(iii) F1: DRSHLSR (SEQ ID NO:34);
F2: TSGSLTR (SEQ ID NO:35);
F3: RSDSLSA (SEQ ID NO:14);
F4: DRSSRTK (SEQ ID NO:15);
F5: RSDNLSE (SEQ ID NO:36); and F6: HSNARKT (SEQ ID NO:37); and wherein the protein binds to the target sequence shown in SEQ ID NO:33;
(iv) F1: RSDNLSV (SEQ ID NO:39);
F2: DRSNLTR (SEQ ID NO:40);
F3: RSDTLSE (SEQ ID NO:41); and
F4: RSQTRKT (SEQ ID NO:42); and wherein the protein binds to the target sequence shown in SEQ ID NO:38;
(v) F1: QNAHRKT (SEQ ID NO:50);
F2: QSGDLTR (SEQ ID NO: 53);
F3: QSGDLTR (SEQ ID NO:53);
F4: QSSNLAR (SEQ ID NO:54); and
F5: TSSNRKT (SEQ ID NO: 55); and wherein the protein binds to the target sequence shown in SEQ ID NO:52;
(vi) F1: RSDNLAR (SEQ ID NO:57);
F2: QSGDLTR (SEQ ID NO: 53);
F3: DNRQLIT (SEQ ID NO:58);
F4: TSSNLSR (SEQ ID NO:8);
F5: RSDTLSR (SEQ ID NO:59); and
F6: RNDDRIT (SEQ ID NO:60); and wherein the protein binds to the target sequence shown in SEQ ID NO:56;
(vii) F1: RSDNLTT (SEQ ID NO:62);
F2: RSDHLSR (SEQ ID NO:63);
F3: QSSDLRR (SEQ ID NO:64);
F4: QSSHLTR (SEQ ID NO:3); and
F5: RSDHLTQ (SEQ ID NO:65); and wherein the protein binds to the target sequence shown in SEQ ID NO:61;
(viii) F1: QSGSLTR (SEQ ID NO:67);
F2: TSSNRKT (SEQ ID NO:55);
F3: DRSHLTR (SEQ ID NO:68);
F4: RSDDRKT (SEQ ID NO:69);
F5: NRTDLIR (SEQ ID NO:7); and
F6: TSSNLSR (SEQ ID NO:8); and wherein the protein binds to the target sequence shown in SEQ ID NO:66;
(ix) F1: RSDHLST (SEQ ID NO:1);
F2: DRSHLAR (SEQ ID NO:2);
F3: QSSHLTR (SEQ ID NO:3); and
F4: RSDNLRE (SEQ ID NO:4); and wherein the protein binds to the target sequence shown in SEQ ID NO:1;
(x) F1: RSANLSV (SEQ ID NO:5);
F2: DRANLSR (SEQ ID NO:6);
F3: NRTDLIR (SEQ ID NO:7); and
F4: TSSNLSR (SEQ ID NO:8); and wherein the protein binds to the target sequence shown in SEQ ID NO:22;
(xi) F1: DRSDLSR (SEQ ID NO:45);
F2: NRTDLIR (SEQ ID NO:7);
F3: TSSNLSR (SEQ ID NO:8);
F4: RSDTLSQ (SEQ ID NO:46); and
F5: DRSARTR (SEQ ID NO:47); and wherein the protein binds to the target sequence shown in SEQ ID NO:44; and
(xii) F1: RSDALSV (SEQ ID NO:48);
F2: DSSHRTR (SEQ ID NO:49);
F3: QNAHRKT (SEQ ID NO:50);
F4: RSDHLST (SEQ ID NO:1); and
F5: TSGHLSR (SEQ ID NO:51) and wherein the protein binds to the target sequence shown in SEQ ID NO:44.

2. A fusion protein comprising a zinc finger DNA-binding domain according to claim 1 and a FokI cleavage half-domain.

3. The fusion protein of claim 2, wherein the FokI cleavage half-domain is a wild-type Fold cleavage half-domain.

4. The fusion protein of claim 2, wherein the FokI cleavage half-domain is an engineered Fold cleavage half-domain.

5. A polynucleotide encoding the zinc finger DNA-binding domain according to claim 1.

6. An isolated cell comprising a protein according to claim 1.

7. A method of inactivating an endogenous cellular BAK or BAX gene in a cell, the method comprising:
(a) introducing, into a cell, a first nucleic acid encoding a first fusion protein according to claim 2,
(b) introducing, into the cell, a second nucleic acid encoding a second fusion protein according to claim 2, whereby the first and second fusion proteins bind to and dimerize to cleave at least one of the BAK and BAX genes.

8. The method of claim 7, wherein the first and second fusion proteins are encoded by the same nucleic acid.

9. The method of claim 7, wherein the first and second fusion proteins are encoded by different nucleic acids.

10. A method of producing a recombinant protein of interest in a host cell, the method comprising the steps of:
(a) providing a host cell comprising endogenous BAX and BAK genes;
(b) inactivating one or both of the endogenous BAX and BAK genes of the host cell by the method of claim 7; and
(c) introducing an expression vector comprising a transgene, the transgene comprising a sequence encoding a protein of interest into the host cell, thereby producing the recombinant protein.

11. The method of claim 10, wherein the protein of interest comprises an antigen.

12. The method of claim 11, wherein the antigen comprises an influenza antigen.

13. A cell line in which at least one of Bak and Bax are partially or fully inactivated, wherein the cell line is produced by
(a) inactivating at least one of Bak and Bax in a cell according to the method of claim 7; and
(b) culturing the cell under conditions suitable for generating a cell line in which at least one of Bak and Bax is partially or fully inactivated.

14. The cell line of claim 13, wherein the cell is a mammalian cell selected from the group consisting of a COS cell, a CHO cell, a VERO cell, a MDCK cell, a WI38 cell, a V79 cell, a B14AF28-G3 cell, a BHK cell, a HaK cell, a NS0 cell, a SP2/0-Ag14 cell, a HeLa cell, an HEK293 cell, and a perC6 cell.

15. The method of claim 7, wherein the first and second fusion proteins form a homodimer.

16. The method of claim 7, wherein the first and second fusion proteins form a heterodimer.

* * * * *